United States Patent [19]
Mukouyama et al.

[11] Patent Number: 6,150,142
[45] Date of Patent: Nov. 21, 2000

[54] PROCESS FOR PRODUCTION OF L-ASPARTIC ACID

[75] Inventors: Masaharu Mukouyama; Satomi Komatsuzaki, both of Ibaraki, Japan

[73] Assignee: Nippon Shokubai Co., Ltd., Osaka, Japan

[21] Appl. No.: 09/249,336

[22] Filed: Feb. 12, 1999

[30] Foreign Application Priority Data

Feb. 13, 1998 [JP] Japan ................................. 10-031857
Feb. 13, 1998 [JP] Japan ................................. 10-031858

[51] Int. Cl.$^7$ ............................. C12P 13/20; C12N 11/08
[52] U.S. Cl. ........................................... 435/109; 435/180
[58] Field of Search .................................... 435/109, 180

[56] References Cited

U.S. PATENT DOCUMENTS

| | | | |
|---|---|---|---|
| 5,488,155 | 1/1996 | Brun et al. | 562/554 |
| 5,541,090 | 7/1996 | Sakano | 435/109 |
| 5,783,428 | 7/1998 | Goto et al. | 435/109 |
| 5,939,296 | 8/1999 | Sakano et al. | 435/145 |

FOREIGN PATENT DOCUMENTS

| | | |
|---|---|---|
| 0 588 674 A1 | 3/1994 | European Pat. Off. . |
| 48-56618 | 8/1973 | Japan . |
| 2524306 | 8/1994 | Japan . |
| 2804004 | 2/1996 | Japan . |
| 2804005 | 2/1996 | Japan . |

OTHER PUBLICATIONS

Woods et al., Structural and Functional Relationships Between Fumarase and Aspartase, Biochem. J.—vol. 237, pp. 547–557 (1986).

Sakano Koichi, "Production of L–Aspartic Acid", Patent Abstracts of Japan, Pub. No. 07308195, Nov. 28, 1995.

Sakano Koichi, "Production of L–Aspartic Acid", Patent Abstracts of Japan, Pub. No. 07313178, Dec. 5, 1995.

Iwane Hiroshi, "Production of Aqueous Solution of L–Aspartic Acid Alkali or Alkaline Earth Metal Salt", Patent Abstracts of Japan, Pub. No. 10337195, Dec. 22, 1998.

*Primary Examiner*—Herbert J. Lilling
*Attorney, Agent, or Firm*—Finnegan, Henderson, Farabow, Garrett & Dunner, L.L.P.

[57] ABSTRACT

A process for producing crystalline L-aspartic acid is disclosed essentially consisting of the steps of preparing a mix solution containing fumaric acid, ammonia and an alkaline metal hydroxide, reacting the mix solution with aspartase to give a reaction solution containing L-aspartate and crystallizing L-aspartic acid out of the reaction solution, wherein a further amount of ammonia is added to the reaction solution containing L-aspartate and subsequently fumaric acid is added thereto to crystallize L-aspartic acid. The process can provide crystalline L-aspartic acid of high purity in a good workability without the need of any complicated steps.

12 Claims, No Drawings

PROCESS FOR PRODUCTION OF L-ASPARTIC ACID

BACKGROUND OF THE INVENTION

1. Field of the Invention

The present invention relates to a process for production of crystalline L-aspartic acid from fumaric acid with aspartase. The present invention also relates to a method for recycling the non-crystallized L-aspartic acid remaining in the mother liquor given after isolating the crystalline L-aspartic acid, by adding to the starting solution for the subsequent reaction.

2. Description of the Prior Art

A process for crystallizing and collecting a DL-aspartic acid has been disclosed in Japanese Patent Application Laid-open No. 48-56618 in which fumaric acid is added to a disodium DL-aspartate solution. This process comprises reacting disodium fumarate with a large excess of ammonia to form a DL-aspartic acid, expelling the excess ammonia from the reaction solution, and then adding fumaric acid to the reaction solution to crystallize and isolate a DL-aspartic acid.

In this process, the solution before the addition of fumaric acid is a solution of sodium DL-aspartate, to which fumaric acid is added to precipitate a DL-aspartic acid. The mother liquor (i.e., the filtrate) after the isolation of crystalline DL-aspartic acid is a solution of disodium fumarate. Subsequently, a large excess amount of ammonia based on the amount of fumaric acid is added to the disodium fumarate solution, which is recycled in turn as the starting solution for the subsequent reaction.

In general, in the reaction for producing an L-aspartic acid from ammonium fumarate with enzyme, addition of ammonia in an amount equimolar with the amount of the starting material (i.e., fumaric acid) or more is required. For shifting the equilibrium of the reaction to the L-aspartic acid side, ammonia is usually used in an amount of from 2 to 2.3 times the molar amount of fumaric acid. On the other hand, aspartase, the enzyme catalyzing the reaction, has the optimum pH of about 8.3. In a pH range too much higher than this pH value, the enzymatic activity is likely to be reduced disadvantageously.

In the process disclosed in Japanese Patent Application Laid-open No. 48-56618, a large excess amount of ammonia is added to the disodium fumarate solution for recycling. The disodium fumarate solution has a pH of 8.4. When ammonia is added to this solution in the equimolar amount with the amount of fumaric acid, the pH of the solution rises to 12.1 at 30° C., at which pH aspartase is denaturated. Therefore, the addition of such amount of ammonia is not suitable for the enzymatic reaction with aspartase.

Japanese Patent No. 2524306 has disclosed a process for crystallization and isolation of L-aspartic acid by adding fumaric acid to a monoammonium L-aspartate solution. In this process, a solution of diammonium fumarate is converted into a solution of monoammonium L-aspartate with aspartase, fumaric acid is added to the resultant solution to crystallize L-aspartic acid, which is isolated by filtration, and then ammonia is added to the filtrate for the subsequent reaction.

In this process, the salt exchange reaction between L-aspartic acid and fumaric acid is conducted under a heterogeneous condition where crystals of either fumaric acid or L-aspartic acid or both are present, since fumaric acid is added to the monoammonium L-aspartate solution.

Furthermore, in this process, the amount of fumaric acid first added is 0.5 times the molar amount of the L-aspartate present in the reaction solution. However, for recycling the reaction solution after isolating crystalline L-aspartic acid as the starting solution for the subsequent reaction, an additional amount of fumaric acid must be supplemented to the reaction solution to re-adjust the reduced substrate concentration to the initial one. That is, addition of a solid component (i.e., fumaric acid) is conducted twice. Increase in the number of such a complicated step of handling a solid component in a process may result in a poor workability and a poor purity of the L-aspartic acid yielded.

SUMMARY OF THE INVENTION

Accordingly, the object of the present invention is to solve the above-mentioned problems and to provide a process for producing crystalline L-aspartic acid of high purity by the action of aspartase.

We have intensively studied to solve the above-mentioned problems. As a result, we have now found the following: when the amount of fumaric acid added for crystallization of L-aspartic acid is around equimolar with that of L-aspartate present in the ammonium L-aspartate solution, the fumarate formed after addition of the fumaric acid is monoammonium fumarate, which generally shows a small solubility; and a part of the monoammonium fumarate appears as crystals in the solution and included into the crystals of L-aspartic acid as impurities; thus, the purity of the crystalline L-aspartic acid is reduced.

In order to improve this defect, we have found a method for producing crystalline L-aspartic acid, in which ammonia is added to an ammonium L-aspartate solution which is obtained by the enzymatic reaction with aspartase to bring the reaction solution into a state where ammonia is dissolved in excess, and then fumaric acid is added to the reaction solution in an amount of from 0.6 to 1.2 times the total molar amount of fumarate and L-aspartate both present in the reaction solution so that the fumaric acid is dissolved to the solution and L-aspartic acid is crystallized out of the solution.

We have found another method for producing crystalline L-aspartic acid, in which ammonia is added to an ammonium L-aspartate solution which is obtained by the enzymatic reaction with aspartase, the reaction solution is heated, fumaric acid is added to the heated reaction solution to accelerate the dissolution of the fumaric acid thereto, the resultant homogeneous solution without crystals is then cooled to crystallize only L-aspartic acid out of the solution.

In these approaches, by the addition of ammonia to the reaction solution, not monoammonium fumarate alone but a mixture of monoammonium fumarate and diammonium fumarate can be produced after addition of fumaric acid. The diammonium fumarate, due to its high solubility, is not included into the crystals of L-aspartic acid. With respect to the monoammonium fumarate that is produced as a part of the reaction products, the concentration in the reaction solution decreases by the formation of diammonium fumarate and, therefore, it is present in the reaction solution in a completely dissolved state. Consequently, because the inclusion of crystals of monoammonium fumarate into the crystalline L-aspartic acid can be prevented, crystals of L-aspartic acid can be obtained with a high purity.

Furthermore, we have also found that the yield of the crystalline L-aspartic acid can be increased by using the combination of ammonia and an alkaline metal hydroxide (e.g., sodium hydroxide) for neutralization of the substrate solution for aspartase (i.e., the starting fumaric acid solution), and that the amount of the alkaline metal hydroxide added has the optimum range for the enzymatic reaction with aspartase.

Based on the above-mentioned findings, we have accomplished the invention.

Therefore, according to one aspect of the present invention, there is provided a process for producing crystalline L-aspartic acid comprising the steps of preparing a mix solution comprising fumaric acid, ammonia and an alkaline metal hydroxide, reacting the mix solution with aspartase to give a reaction solution containing L-aspartate and crystallizing L-aspartic acid out of the reaction solution, wherein a further amount of ammonia is added to the reaction solution containing L-aspartate and subsequently fumaric acid is added thereto to crystallize L-aspartic acid.

Here, the non-crystallized aspartic acid remaining in the reaction solution after the crystallization of L-aspartic acid may be isolated, ammonia may be added to the solution, and the resultant solution may be recycled as a part of the starting reaction solution for the process of producing crystalline L-aspartic acid.

According to another aspect of the present invention, there is provided a process for producing crystalline L-aspartic acid comprising the steps of preparing a mix solution comprising fumaric acid, ammonium L-aspartate, ammonia and an alkaline metal hydroxide, reacting the mix solution with aspartase to give a reaction solution containing L-aspartate and crystallizing L-aspartic acid out of the reaction solution, wherein a further amount of ammonia is added to the reaction solution containing L-aspartate and subsequently fumaric acid is added thereto to crystallize L-aspartic acid.

According to another aspect of the present invention, there is provided a process for producing crystalline L-aspartic acid comprising the steps of preparing a mix solution comprising fumaric acid, ammonia and an alkaline metal hydroxide, reacting the mix solution with aspartase to give a reaction solution containing L-aspartate and crystallizing L-aspartic acid out of the reaction solution, wherein a further amount of ammonia is added to the reaction solution containing L-aspartate, the reaction solution is heated, fumaric acid is added to the reaction solution, and the reaction solution is cooled to crystallize L-aspartic acid.

Here, the non-crystallized aspartic acid remaining in the reaction solution after the crystallization of L-aspartic acid may be isolated, ammonia may be added to the solution, and the resultant solution may be recycled as a part of the starting reaction solution for the process of producing crystalline L-aspartic acid.

According to another aspect of the present invention, there is provided a process for producing crystalline L-aspartic acid comprising the steps of preparing a mix solution comprising fumaric acid, ammonium L-aspartate, ammonia and an alkaline metal hydroxide, reacting the mix solution with aspartase to give a reaction solution containing L-aspartate and crystallizing L-aspartic acid out of the reaction solution, wherein a further amount of ammonia is added to the reaction solution containing L-aspartate, the reaction solution is heated, fumaric acid is added thereto to the reaction solution, and the reaction solution is cooled to crystallize L-aspartic acid.

Here, the amount of the alkaline metal hydroxide in the mix solution may be from 0.1 to 1 times the total molar amount of fumarate and L-aspartate both contained in the solution.

The amount of the fumaric acid added for crystallization of L-aspartic acid may be from 0.6 to 1.2 times the total molar amount of fumarate and L-aspartate both contained in the reaction solution containing L-aspartic acid.

The aspartase may be an immobilized aspartase prepared by immobilizing a transformant carrying an aspartase gene or a product from the transformant onto a carrier.

The mix solution comprising fumaric acid, L-aspartic acid, ammonia and an alkaline metal hydroxide which contains fumaric acid and L-aspartic acid in a concentration of 8 to 20% in terms of fumaric acid may be made to flow through a reactor containing an immobilized aspartase having an aspartase activity of 250 U of the carrier or more at a liquid hour space velocity of 2 to 20. Here, "1 U" means 1 μmole L-aspartic acid yielded/min/ml immobilized aspartase and "liquid hour space velocity (LHSV)" means volume of solution flowed (ml)/volume of catalyst packed (ml) per hour.

The immobilized aspartase may be prepared by adsorption of microorganism cells having an aspartase activity or products from the microorganism cells onto an ion exchange resin or by coating of a polymer containing the microorganism cells or the products from the microorganism cells onto the ion exchange resin.

The immobilized aspartase may be prepared by mixing microorganism cells having an aspartase activity or products from the microorganism cells with a polymer of formula (I) and then coating the mixture onto the surface of the spherical styrene/divinylbenzene copolymer ion exchange resin particles:

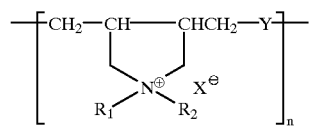

wherein Y denotes a direct bonding or a divalent group selected from the group consisting of $$-\underset{\underset{O}{\overset{\overset{O}{\|}}{S}}}{-} \quad \text{or} \quad -\underset{\underset{COOH}{|}}{CH}-\underset{\underset{COOH}{|}}{CH}- \;;$$

each of $R_1$ and $R_2$ is independently a hydrogen atom or an organic residue; $X^{\ominus}$ denotes an anion; and n is an integer from 100 to 5000.

This specification includes part or all of the contents as disclosed in the specifications and/or drawings of Japanese Patent Applications No. 10-31857 and 10-31858, which are priority documents of the present application.

DETAILED DESCRIPTION OF THE INVENTION

Hereafter, The present invention will be described in detail.

In the present invention, aspartase may be used in a form of an aspartase-containing material having an aspartase activity. Examples of the aspartase-containing material include cells of microorganisms known to have a high aspartase activity, such as *Escherichia coli* and microorganisms belonging to the families Brevibacterium and Pseudomonas, and products thereof produced by, for example, ultrasonification, attrition, freeze-thawing, treatment with an enzyme or a surfactant of the cells. The aspartase may also be partially purified from the cell products by a conventional technique such as ammonium sulfate fraction and acetone precipitation, or may be completely purified from the cell products by a conventional technique such as chromatography. Any type of aspartase can be used as long as it exhibits an aspartase activity.

However, in the present invention, it is particularly preferable to use a recombinant *E. coli* cell that has been transformed with a plasmid carrying an aspartase gene so that it can produce aspartase in an increased amount. This is because when an alkaline metal hydroxide (e.g., sodium hydroxide) is used for neutralization of fumaric acid in part, the amount of ammonia in the reaction solution is reduced relative to the amount of the alkaline metal hydroxide, resulting in decrease in a conversion rate of fumaric acid into L-aspartic acid.

The aspartase gene which can be used in the present invention may be derived from any microorganism whose gene is known to naturally cross with *E. coli* gene and which has an aspartase activity, including *E. coli, Pseudomonas fluorescens* and microorganisms belonging to the families Enterobacter and Citrobacter. The aspartase gene can be obtained from, for example, the chromosome DNA of *E. coli* strain K-12 (IFO 3301) or *Pseudomonas fluorescens* (IFO 3081) and amplified by polymerase chain reaction (PCR) using primers prepared based on a known aspartase gene sequence.

The plasmid to which the aspartase gene is integrated is not particularly limited, and any one may be used as long as it can be replicated in a microorganism belonging to *E. coli*. Examples of the plasmid include pUC18 and pKK223-3. The host microorganism into which the plasmid carrying the aspartase gene is introduced is preferably *E. coli* strain K-12.

In the present invention, a microorganism cell having an aspartase activity, a product thereof or aspartase itself may be immobilized in a carrier in a conventional manner. Examples of the carrier include natural polymers such as cellulose, alginic acid, carageenan and mannan gel; and synthetic polymers such as ion exchange resins, poly(vinyl alcohol), polyacrylamide. Among these, preferably is a spherical ion exchange resin particle made of styrene/divinylbenzene copolymer, onto which a mixture of a polymer of the formula (I) above with the above-mentioned microorganism cells or the product thereof is coated. For example, it is preferable to immobilize the microorganism cells onto a water-insoluble carrier by coating a mixture of the cells with a water-soluble polymer (e.g., PAS-880) which is capable of forming a crosslinkage between the polymer molecules or between the polymer and the surface of the cells onto the carrier and then drying the coating.

The immobilized aspartase prepared in this manner exhibits a low pressure loss and a low diffusion barrier due to its thin diffusion layer, and therefore is suitable for a reaction with a high liquid hour space velocity (LHSV).

The starting substrate solution used in the present invention is an aqueous solution of fumaric acid and a fumaric acid-neutralizing salt. The alkali used is a combination of ammonia and an alkali metal hydroxide. The amount of the alkali metal hydroxide is within the range from 0.1 to 1.2 times, preferably from 0.3 to 1.0 times, and more preferably from 0.4 to 0.8 times the total molar amount of L-aspartate and fumarate present in the substrate solution. Here, it would be easily understood by the persons skilled in the art that the expression "the total molar amount of L-aspartate and fumarate present in the substrate solution" means "the molar amount of fumarate present in the substrate solution" at the initial state where L-aspartate is not present in the substrate solution, which is actually the molar amount of "fumaric acid" itself added to the substrate solution. From the nature of the present invention where the recycling of the substrate solution is taken into account, the expression is used throughout the present specification for convenience. The same goes for the expression for the amount of ammonia mentioned below. If the amount of the alkali metal hydroxide is below the range, the recovery of crystalline L-aspartic acid decreases. Whereas if the amount of the alkaline metal hydroxide is beyond the range, the pH value of the substrate solution becomes too high and the amount of ammonia added decreases, resulting in a decreased conversion rate of fumaric acid into L-aspartic acid as well as the possibility of inactivation of aspartase.

The ammonia used in the present invention is preferably in a form of an aqueous solution in view of industrial applicability. However, liquid ammonia and ammonia gas may also be used. The amount of ammonia in the starting substrate solution is within the range from 1 to 2 times, preferably from 1.1 to 1.8 times, and more preferably from 1.2 to 1.5 times the total molar amount of L-aspartate and fumarate in the substrate solution. In the present invention, it is preferable to add ammonia to the substrate solution in such an amount after addition of the alkali metal hydroxide in order to adjust the resultant substrate solution to a pH within the range from 6 to 9.5, preferably from 7 to 9.3, and more preferably from 8 to 9. The concentration of fumaric acid in the starting substrate solution is preferably 5–20% by weight. However, in view of productivity and purity of the crystalline L-aspartic acid yielded, it is particularly effective to use fumaric acid in a concentration of 8–15% by weight.

The substrate solution may additionally contain a divalent metal salt such as a manganese salt, e.g., manganese chloride, manganese sulfate; a magnesium salt, e.g., magnesium chloride, magnesium sulfate; and a cobalt salt, in a concentration of 0.1–50 mM, and preferably 1–10 mM.

In the present invention, any type of reactor may be employed, including conventional reactors of batch type or column type. The reactor may be used singly or in combination of two or more thereof.

In order to produce crystalline L-aspartic acid in an industrial large scale, a column-type reactor is particularly preferable. In the reaction carried out in a column-type reactor, when an immobilized aspartase is used which is prepared by coating a mixture of a polymer of formula (I) with *E. coli* cells which have been transformed with a plasmid carrying aspartase gene so as to produce aspartase in an increased amount onto spherical particles of styrene/divinylbenzene copolymer ion exchange resin, the substrate solution may be passed through the column at a flow rate LHSV of 2–20 to cause to react the solution with aspartase.

When an immobilized aspartase in which natural *E. coli* cell is immobilized is used, it is required to extend the reaction period or decrease the flow rate (LHSV) of the substrate solution since the aspartase activity of natural *E. coli* is not so high. In contrast, when an immobilized aspartase in which *E. coli* cell transformed with aspartase gene is used, a satisfactory conversion rate can be attained even at the above-mentioned flow rate since such immobilized aspartase has an extremely high aspartase activity.

The reaction temperature is preferably within the range from about 10° C. to about 50° C., and more preferably within the range from 15° C. to 40° C. With the reaction temperature lower than this range, the reaction rate tends to decrease. Whereas with the reaction temperature beyond this range, the aspartase activity is likely to be inactivated.

The reaction of fumaric acid with ammonia is conducted under the conditions described above. Although it is preferable to proceed the reaction at a higher conversion rate, the conversion rate of about 90% is satisfactory for the subsequent crystallization of L-aspartic acid, even if the reaction does not reach equilibrium.

Next, ammonia is added to the reaction solution to adjust the pH of the solution to pH 9 or more, preferably pH 9.1 or more, and more preferably pH 9.3 or more. The upper limit of the amount of ammonia added is equimolar with the total amount of fumarate and L-aspartate present in the reaction solution, particularly from 0.1 to 0.9 times, more preferably from 0.3 to 0.7 times the total molar amount of fumarate and L-aspartate present in the reaction solution. With ammonia in an amount lower than the range, contamination of monoammonium fumarate into the crystalline L-aspartic acid occurs. Whereas with ammonia in an amount beyond the range, the yield of crystalline L-aspartic acid is reduced.

In one aspect of the present invention, after addition of ammonia, fumaric acid is further added to the reaction solution. The amount of the fumaric acid is within the range from 0.6 to 1.2 times, preferably from 0.7 to 1.1 times, and more preferably from 0.8 to 1.0 times the total molar amount of fumarate and L-aspartate present in the reaction solution. When fumaric acid is added in an amount lower than the range, the yield of crystalline L-aspartic acid is reduced. Whereas when fumaric acid is added in an amount beyond the range, contamination of fumarates into the crystalline L-aspartic acid occurs.

After addition of fumaric acid, the reaction solution is stirred at a temperature of 45° C. or less. If the temperature is too low, crystals of monoammonium fumarate which have a low solubility are likely to be included into the crystalline L-aspartic acid. Therefore, the temperature of the reaction solution is preferably 10–40° C., and more preferably 25–35° C. After addition of fumaric acid, stirring of the reaction solution is allowed to continue for 1 sec to 1 hour, preferably 1 to 15 min, to complete the crystallization of L-aspartic acid out of the solution. The crystallized L-aspartic acid may be isolated from the solution by a conventional means such as suction filtration and centrifugal filtration. Centrifugal filtration is preferable because it can give the cake of crystalline L-aspartic acid of a low liquid content.

In another aspect of the present invention, after addition of ammonia, the reaction solution is heated to 45° C. or more, preferably 50° C. or more. Although the heating temperature does not have a particular upper limit, the reaction solution is usually heated to a temperature up to the boiling point thereof under normal pressures. Subsequently, fumaric acid is added to the heated reaction solution. The amount of the fumaric acid added is within the range from 0.6 to 1.2 times, preferably from 0.65 to 1.1 times, and more preferably from 0.7 to 1.0 times the total molar amount of fumarate and L-aspartate present in the reaction solution. When the amount of fumaric acid is below the range, the yield of the crystalline L-aspartic acid decreases. Whereas when the amount of fumaric acid is beyond the range, a fumarate is included into the crystalline L-aspartic acid. After fumaric acid is added, the reaction solution is stirred at a temperature of 45° C. or more for 1 sec to 1 hour, preferably 1 to 15 min to dissolve fumaric acid completely. This solution is a homogeneous solution containing no crystals of fumaric acid or L-aspartic acid. The reaction solution is then cooled to crystallize L-aspartic acid out of the solution. The cooling is continued until the temperature of the suspension (i.e., a solution containing crystalline L-aspartic acid) reaches a temperature range from 10–45° C. When the temperature is beyond the range, the yield of crystalline L-aspartic acid decreases. Whereas when the temperature is below the range, fumarate is included into the crystalline L-aspartic acid.

After cooling, the solution is stirred for additional 1 sec to 1 hour, preferably 5 to 15 min, to complete the crystallization of L-aspartic acid out of the solution. The yielded crystalline L-aspartic acid may be isolated from the solution by a conventional means such as suction filtration and centrifugal filtration. Centrifugal filtration is preferable since it can give a cake of crystalline L-aspartic acid of a low liquid content.

The crystals of L-aspartic acid thus isolated (i.e., a cake) may be washed with water, if necessary. By washing, the amount of the fumarate included into the crystals of L-aspartic acid in a small amount can be reduced, resulting in a high purity of the crystalline L-aspartic acid. However, in view of recycling the mother liquor after isolating the crystals of L-aspartic acid from the solution, it is not preferable to wash the crystals with a very large volume of water. The amount of water for washing the crystals is within the range from 5 to 500% by weight, and preferably from 10 to 200% by weight, based on the amount of the crystals of L-aspartic acid. In this manner, crystalline L-aspartic acid containing a trace amount, for example 0.1 to 3% by weight, preferably 0.2 to 2% by weight, of fumarate can be obtained. The fumarate-containing crystalline L-aspartic acid thus obtained is hardly airborne even if it is made into fine powder and, therefore, is easy to handle and extremely useful as the L-aspartic acid for industrial use.

The L-aspartic acid can be used as an additive for food, medicines and the like by further repeated purification.

The mother liquor after isolating the crystals of L-aspartic acid may be recycled as the starting substrate solution for the subsequent reaction by mixing with the wash solution of the cake and adding ammonia thereto. If necessary, the mother liquor and the wash solution may be subjected to an appropriate treatment such as concentration. For example, the volume of the substrate solution increases by the volume of the water from the wash solution and the aqueous ammonia solution. Therefore, after addition of ammonia, the total volume of the substrate solution can be adjusted to the predetermined initial volume by concentrating the mother liquor and the wash solution. The molar amount of ammonia supplemented can be determined by subtracting the molar amount of ammonia added prior to the addition of fumaric acid from the molar amount of L-aspartic acid isolated as crystals. Thus, the amount of ammonia in the substrate solution is adjusted to from 1 to 2 times the total molar amount of fumarate and L-aspartate present in the solution. This solution has a pH within the range from 6 to 11. In this manner, the mother liquor can be prepared into the starting substrate solution for the subsequent reaction. That is, in an aspect of the invention, a series of procedures is repeated which comprises the steps of reacting the substrate solution with an aspartase-containing material having an aspartase activity, adding ammonia to the reaction solution, adding fumaric acid to the reaction solution to crystallize L-aspartic acid out of the solution, isolating the crystals of L-aspartic acid, and preparing the next starting substrate solution from the mother liquor. In another aspect of the invention, a series of procedures is repeated which comprises the steps of reacting the substrate solution with an aspartase-containing material having an aspartase activity, adding ammonia to the reaction solution, heating the reaction solution, adding fumaric acid to the warm reaction solution, cooling the reaction solution to crystallize L-aspartic acid out of the solution, isolating the crystals of L-aspartic acid, and preparing the next starting substrate solution from the mother liquor. According to the present invention, it is possible to recycle the mother liquor 10 times or more.

The preparation process of aspartase derived from *E. coli* by genetic engineering technique is described below.

(i) Production of *E. coli* Transformant with Recombinant Aspartase Gene

Cells of *E. coli* strain IFO3301 purchased from Institute for Fermentation were inoculated to a LB medium of Table 1 below and cultured at 37° C. for 8 hours. Cells were collected from 1 ml of the culture and suspended to 1 ml of distilled water. 1 µl of the cell suspension was used as the template DNA for amplification of aspartase gene.

TABLE 1

| Composition of LB medium | |
|---|---|
| Polypeptone | 10 g |
| Yeast extract | 5 g |
| NaCl | 10 g |
| Distilled water | 1 L |
| (autoclaved at 121° C. for 15 min) | |

(ii) Amplification of Aspartase Gene by PCR and Production of Insert Fragments

Based on the known sequence of aspartase gene of *E. coli* strain K-12 (SEQ.ID NO: 1) (Biochem. J. 237 (2), 547–557), the two primers below were produced for amplification of *E. coli* aspartase gene.

Primer F: GGATAATCGTCGGTCGAAAA
Primer R: CGTCATCTGACGTGCCTTT

A reaction solution of the composition below was prepared using KOD DNA polymerase (Toyobo Co., Ltd.) for amplification of the aspartase gene by PCR.

| | |
|---|---|
| 10X Buffer | 5 µl |
| dNTPs Mix | 5 µl |
| MgCl$_2$ | 2 µl |
| Template DNA | 1 µl |
| KOD DNA polymerase | 1 µl |
| Primer F (25 pmol) | 1 µl |
| Primer R (25 pmol) | 1 µl |
| Sterilized water | 34 µl |
| Total | 50 µl |

Conditions for PCR

| | |
|---|---|
| ① 98° C. | 5 min. |
| ② 98° C. | 30 sec. |
| ③ 53° C. | 30 sec. |
| ④ 68° C. | 1 min. |
| (repeating from ② through ④ for 30 cycles) | |

After the PCR was completed, the amplified DNA fragment was subjected to electrophoresis on a 1% agarose gel and the gel was stained with ethidium bromide. As a result, it was confirmed that the predicted fragment of about 1600 bp was amplified.

The portion containing the DNA fragment was excised from the agarose gel and the DNA fragment was collected therefrom using Prep-A-Gene (Bio-Rad Laboratories Inc.).

(iii) Ligation of the Insert Fragment to a Vector

The above-obtained DNA fragment was ligated with a pCR-Script Amp SK(+) cloning vector in the presence of a restriction enzyme Srf and a DNA ligase.

The transformant carrying the vector containing the insert DNA fragment was designated strain PUaspE1.

The strain PUaspE1 was inoculated to 3 ml of a LB medium supplemented with 100 ppm of ampicillin and then cultured with shaking at 37° C. overnight, and the cells were collected from 1.5 ml of the culture. The cells were subjected to alkaline SDS method to collect plasmids therefrom. The plasmid thus obtained was designated pUaspE1.

This plasmid was analyzed on the nucleotide sequence of the insert fragment. As a result, it was found that the aspartase gene was inserted in the reverse direction relative to the promoter of the vector.

In order to re-ligate the insert fragment in the forward direction relative with the promoter, the plasmid pUaspE1 was digested with SacI and BamHI to cleave out the insert fragment and the fragment was introduced into plasmid pUC19. That is, the plasmid pUaspE1 was digested with BamHI and then subjected to ethanol precipitation to collect DNA fragments. The DNA fragments were further digested with SacI and the resultant was subjected to electrophoresis on a 1% agarose gel to isolate the DNA fragments. The portion containing the DNA fragments was excised from the gel and the DNA was collected with Prep-A-Gene (Bio-Rad Laboratories Inc.)

(iv) Production of a Vector

1 µg of plasmid pUC19 (Nippon Gene Co., Ltd.) was digested with BamHI and then subjected to ethanol precipitation to collect DNA fragments. The DNA fragments were further digested with SacI. The resultant DNA fragments were isolated by electrophoresis on a 1% agarose gel and the portion containing the DNA fragments was excised from the gel to collect the DNA with Prep-A-Gene (Bio-Rad Laboratories Inc.). The collected DNA was used as a vector.

(v) Ligation of the Insert Fragment to the Vector

The insert fragment was ligated with the vector which had been digested with the restriction enzyme with Ligation High (Toyobo Co., Ltd.) at 16° C. for 30 min.

(vi) Transformation of *E. coli*

2 µl of the reaction solution containing the insert fragment ligated with the vector was added to 200 µl of competent *E. coli* cells (XL2-Blue MRF' Ultracompetent cells; Stragagene) to transform the *E. coli* cells. The *E. coli* transformants were plated onto a LB agar medium supplemented with 100 ppm of ampicillin and cultured at 37° C. overnight.

20 of the colonies appeared on the medium were picked up, inoculated onto a LB medium supplemented with 100 ppm of ampicillin and then cultured with shaking at 37° C. for 8 hours. Then isopropyl thio-β-D-galactoside (IPTG) was added to the culture in a concentration of 1 mM and further cultured with shaking at 30° C. overnight. The cells were collected from 1 ml of the culture medium.

As a control, *E. coli* cells were transformed with plasmid pUC18 into which the insert fragment was not inserted, plated onto a LB agar medium supplemented with 100 ppm of ampicillin and then cultured at 37° C. overnight in the same manner as mentioned above. One of the colonies of the control transformant appeared on the medium was picked up and cultured and the cells were collected in the same manner as mentioned above.

The cells thus collected were added to 1 ml of the 20% ammonium fumarate substrate solution of Table 2 below, suspended therein and allowed to react at 30° C. for 1 hour.

TABLE 2

Composition of a 20% ammonium fumarate substrate solution

| | |
|---|---|
| Fumaric acid | 200 g |
| Aqueous 25% ammonium solution | 200 g |
| Magnesium sulfate heptahydrate | 2.5 g |
| Ion exchange water | 500 g |
| (adjusted to pH 8.3 with an aqueous 25% ammonium solution and made up with ion exchange water to 1 liter) | |

After the reaction was completed, each of the reaction solutions was analyzed. As a result, it was found that the reaction solution containing the E. coli transformants with the insert fragment showed the conversion rate of fumaric acid into L-aspartic acid of 99.5%, whereas the reaction solution containing the E. coli transformants without the insert fragment showed the conversion rate of only 5%.

One of the transformants with the insert fragment was designated PUaspE2.

The transformant PUaspE2 was inoculated to 3 ml of a LB medium supplemented with 100 ppm of ampicillin and then cultured at 37° C. for 8 hours. Plasmid was collected from 1.5 ml of the culture by alkaline SDS method. The plasmid thus obtained was designated pUaspE2. The plasmid pUaspE2 was digested with SmaI and subsequently with HindIII, and then the size of the resultant fragments was determined by electrophoresis on a 1% agarose gel. As a result, it was found that two fragments of about 2960 bp and about 1600 pb, respectively, were obtained.

The PUaspE2 strain was inoculated to 3 ml of a LB medium supplemented with 100 ppm of ampicillin and cultured with shaking at 37° C. for 8 hours. IPTG was then added to the culture medium in a concentration of 1 mM and the cultivation was continued at 30° C. overnight. The cells were collected from 1 ml of the culture medium. The cell density of the culture determined at $OD_{660nm}$ was 8.0.

The transformant cells thus collected were suspended to 10 ml of a 20% ammonium fumarate substrate solution. The reaction solution was allowed to react at 30° C. for 1 hour and subjected to high performance liquid chromatography (HPLC) analysis. The aspartase activity of the reaction solution determined by calculation with the amount of L-aspartic acid produced and the cell density, was 2000,000 $\mu$M L-aspartic acid yielded/hr/$OD_{660nm}$ cell density.

In the same manner, one colony of the control transformant without the insert fragment was cultured, the cells were collected from the culture, and the cell density of the culture was determined at $OD_{660nm}$. As result, it was found that the cell density of the culture was 8.5.

The control transformant cells thus collected were suspended to 10 ml of a 20% ammonium fumarate substrate solution. The reaction solution was allowed to react at 30° C. for 1 hour and subjected to HPLC analysis. The aspartase activity of the reaction solution determined as above was 10,000 $\mu$M L-aspartic acid yielded/hr/$OD_{660nm}$ cell density.

Accordingly, the transformant PUaspE2 had an aspartase activity of 200 times greater than that of the strain without aspartase gene insert fragment.

(vii) Culture of the Transformant

The recombinant E. coli strain PUaspE2 transfected with E. coli aspartase gene was inoculated into ten test tubes each containing 3 ml of the medium of Table 1 above supplemented with 100 ppm of ampicillin and then cultured at 37° C. for 8 hours. The cultures in the test tubes were respectively inoculated to ten Sakaguchi flasks each containing 100 ml of the same medium of Table 1 above supplemented with 1 mM of IPTG, and cultured at 30° C. overnight. The flasks were centrifuged to collect the cells therefrom. The aspartase activity of the cells from each flask was determined and found to be 1.05 moles L-aspartic acid yielded/hr/g cells.

Preparation of Immobilized Aspartase with the Recombinant E. coli Transfected with Aspartase Gene 70 g of PAS-880 (Nitto Boseki Co., Ltd.) which had been adjusted to about pH 7.0 with an alkali was fully mixed with 230 g of deionized water, and then the recombinant E. coli cells collected in the above step were dispersed homogeneously thereto. To a 6 L-eggplant type flask were added 300 ml of ion exchange resin (AMBERLITE IRA-94S, C1-form, Organo Corporation; average particle diameter: 0.5 mm) and 200 of Teflon beads (particle diameter: 0.5 inch). One-sixth of the cell dispersion solution was added to the flask and then evaporated to dryness for 1 hour while rotating the flask in an evaporator at 30° C. In this manner, the ion exchange resin was coated with the cells. This procedure was repeated 6 times. Thereafter, the Teflon beads were removed to give immobilized aspartase in the form of beads. The enzymatic activity of this immobilized aspartase beads was 3500 U (1 U=1 $\mu$moles L-aspartic acid produced/min/ml immobilized enzyme). The immobilized aspartase beads were hereinafter referred to as "recombinant immobilized aspartase beads" or "recombinant immobilized aspartase" for convenience.

Cultivation of E. coil IFO 3301

E. coli strain IFO 3301 cells which had not been transfected with aspartase gene were cultured in the same manner as mentioned above, except that ampicillin and IPTG were not added to the medium, and cells were collected from the culture.

Preparation of Non-recombinant Immobilized Aspartase

Non-immobilized aspartate was prepared in the same manner as mentioned above, except that E. coli strain IFO 3301 cells obtained above were used. The enzymatic activity of this non-recombinant immobilized aspartase was 180 U (1 U=1 $\mu$moles L-aspartic acid produced/min/ml immobilized enzyme).

The present invention will be further described by illustration in the following Examples, which are not intended to limit the invention.

EXAMPLES

Example 1

The recombinant immobilized aspartase beads prepared with recombinant aspartase gene as mentioned above were soaked in a 20% ammonium fumarate solution (pH 8.3) overnight. 50 ml of the same was packed into a column and the column was externally covered with a thermal insulating material made of foamed polystyrene to maintain the internal temperature of the column constant. A substrate solution of Table 3 (which had been kept at 20° C. in a constant temperature water bath) was fed to the column through a Teflon tube wrapped with a thermal insulating material and made to flow through the column at a flow rate of 500 ml/hr [liquid hour space velocity (LHSV)=10.0]. Thus a continuous reaction was conducted.

3 hours after the reaction was started, the reaction solution was analyzed. As a result, it was found that L-aspartic acid approximately equimolar with the consumed fumaric acid was obtained as a reaction product, where the conversion rate of fumaric acid into L-aspartic acid was 99.2%.

To 1 liter of this reaction solution was added 29.3 g of a 25% aqueous ammonia solution. The reaction solution had a pH of 9.5. 70 g of fumaric acid was added to the reaction solution and stirred for 1 hour to give a suspension containing crystalline L-aspartic acid. At this point, the temperature of the suspension was 30° C. The suspension was filtrated and the resulting cake was fully compressed to remove liquid content therefrom. The cake was washed with 100 ml of water and then dried to give crystalline L-aspartic acid (yield 61.3 g; purity 98.4%).

TABLE 3

| | |
|---|---|
| Fumaric acid | 100 g |
| NaOH | 20 g |
| (0.58 times the molar amount of fumaric acid) | |
| 25% Aqueous ammonia solution | 87.9 g |
| (1.5 times the molar amount of fumaric acid) | |
| Magnesium sulfate | 0.25 g |
| (made up with deionized water to 1 liter). | |

Example 2

The recombinant immobilized aspartase beads as mentioned above were soaked in a 20% ammonium fumarate solution (pH 8.3) overnight. 50 ml of the same was packed into a column and the column was externally covered with a thermal insulating material made of foamed polystyrene to maintain the internal temperature of the column constant. A substrate solution of Table 3 (which had been kept at 20° C. in a constant temperature water bath) was fed to the column through a Teflon tube wrapped with a thermal insulating material and made to flow through the column at a flow rate of 500 ml/hr (LHSV=10.0). Thus a continuous reaction was conducted.

3 hours after the reaction was started, the reaction solution was analyzed. As a result, it was found that L-aspartic acid approximately equimolar with the consumed fumaric acid was obtained as a reaction product, where the conversion rate of fumaric acid into L-aspartic acid was 99.2%.

To 1 liter of this reaction solution was added 29.3 g of a 25% aqueous ammonia solution. The reaction solution had a pH of 9.5. 80 g of fumaric acid was added to the reaction solution and stirred for 1 hour to give a suspension containing crystalline L-aspartic acid. At this point, the temperature of the suspension was 30° C. The suspension was filtrated and the resulting cake was fully compressed to remove liquid content therefrom. The cake was washed with 100 ml of water and then dried to give crystalline L-aspartic acid (yield 72.5 g; purity 98.6%).

Example 3

The recombinant immobilized aspartase beads as mentioned above were soaked in a 20% ammonium fumarate solution (pH 8.3) overnight. 50 ml of the same was packed into a column and the column was externally covered with a thermal insulating material made of foamed polystyrene to maintain the temperature within the column constant. A substrate solution of Table 3 (which had been kept at 20° C. in a constant temperature water bath) was fed to the column through a Teflon tube wrapped with a thermal insulating material and made to flow through the column at a flow rate of 500 ml/hr (LHSV=10.0). Thus a continuous reaction was conducted.

3 hours after the reaction was started, the reaction solution was analyzed. As a result, it was found that L-aspartic acid approximately equimolar with the consumed fumaric acid was obtained as a reaction product, where the conversion rate of fumaric acid into L-aspartic acid was 99.2%.

To 1 liter of this reaction solution was added 29.3 g of a 25% aqueous ammonia solution. The reaction solution had a pH of 9.5. 90 g of fumaric acid was added to the reaction solution and stirred for 1 hour to give a suspension containing crystalline L-aspartic acid. At this point, the temperature of the suspension was 30° C. The suspension was filtrated and the resulting cake was fully compressed to remove liquid content therefrom. The cake was washed with 100 ml of water and then dried to give crystalline L-aspartic acid (yield 84.1 g; purity 98.7%).

Example 4

The recombinant immobilized aspartase beads as mentioned above were soaked in a 20% ammonium fumarate solution (pH 8.3) overnight. 50 ml of the same was packed into a column and the column was externally covered with a thermal insulating material made of foamed polystyrene to maintain the internal temperature of the column constant. A substrate solution of Table 3 (which had been kept at 20° C. in a constant temperature water bath) was fed to the column through a Teflon tube wrapped with a thermal insulating material and made to flow through the column at a flow rate of 500 ml/hr (LHSV=10.0). Thus a continuous reaction was conducted.

3 hours after the reaction was started, the reaction solution was analyzed. As a result, it was found that L-aspartic acid approximately equimolar with the consumed fumaric acid was obtained as a reaction product, where the conversion rate of fumaric acid into L-aspartic acid was 99.2%.

To 1 liter of this reaction solution was added 34.6 g of a 25% aqueous ammonia solution. The reaction solution had a pH of 9.8. 100 g of fumaric acid was added to the reaction solution and stirred for 1 hour to give a suspension containing crystalline L-aspartic acid. At this point, the temperature of the suspension was 30° C. The suspension was filtrated and the resulting cake was fully compressed to remove liquid content therefrom. The cake was washed with 100 ml of water and then dried to give crystalline L-aspartic acid (yield 94.1 g; purity 98.5%).

As is evident from the results of Examples 1–4 above, it is preferable to add fumaric acid in an amount of 70 g or more since a good recovery of 60% or more can be attained.

Example 5

The recombinant immobilized aspartase as mentioned above was soaked in a 20% ammonium fumarate solution (pH 8.3) overnight. 50 ml of the same was packed into a column and the column was externally covered with a thermal insulating material made of foamed polystyrene to maintain the internal temperature of the column constant. A substrate solution of Table 4 (which had been kept at 20° C. in a constant temperature water bath) was fed to the column through a Teflon tube wrapped with a thermal insulating material and made to flow through the column at a flow rate of 500 ml/hr (LHSV=10.0). Thus a continuous reaction was conducted.

3 hours after the reaction was started, the reaction solution was analyzed. As a result, it was found that L-aspartic acid approximately equimolar with the consumed fumaric acid was obtained as a reaction product, where the conversion rate of fumaric acid into L-aspartic acid was 99.2%.

To 1 liter of this reaction solution was added 17.6 g of a 25% aqueous ammonia solution. The reaction solution had a pH of 9.1. 70 g of fumaric acid was added to the reaction solution and stirred for 1 hour to give a suspension containing crystalline L-aspartic acid. At this point, the temperature of the suspension was 30° C. The suspension was filtrated and the resulting cake was fully compressed to remove liquid content therefrom. The cake was washed with 100 ml of water and then dried to give crystalline L-aspartic acid (yield 88.3 g; purity 98.6%).

TABLE 4

| Fumaric acid | 100 g |
|---|---|
| NaOH | 30 g |
| (0.87 times the molar amount of fumaric acid) | |
| 25% Aqueous ammonia solution | 70.0 g |
| (1.2 times the molar amount of fumaric acid) | |
| Magnesium sulfate | 0.25 g |
| (made up with deionized water to 1 liter). | |

Example 6

The recombinant immobilized aspartase as mentioned above was soaked in a 20% ammonium fumarate solution (pH 8.3) overnight. 50 ml of the same was packed into a column and the column was externally covered with a thermal insulating material made of foamed polystyrene to maintain the internal temperature of the column constant. A substrate solution of Table 4 (which had been kept at 20° C. in a constant temperature water bath) was fed to the column through a Teflon tube wrapped with a thermal insulating material and made to flow through the column at a flow rate of 500 ml/hr (LHSV=10.0). Thus a continuous reaction was conducted.

3 hours after the reaction was started, the reaction solution was analyzed. As a result, it was found that L-aspartic acid approximately equimolar with the consumed fumaric acid was obtained as a reaction product, where the conversion rate of fumaric acid into L-aspartic acid was 99.2%.

To 1 liter of this reaction solution was added 17.6 g of a 25% aqueous ammonia solution. The reaction solution had a pH of 9.1. 90 g of fumaric acid was added to the reaction solution and stirred for 1 hour to give a suspension containing crystalline L-aspartic acid. At this point, the temperature of the suspension was 30° C. The suspension was filtrated and the resulting cake was fully compressed to remove liquid content therefrom. The cake was washed with 100 ml of water and then dried to give crystalline L-aspartic acid (yield 97.2 g; purity 98.1%).

Example 7

The non-recombinant immobilized aspartase beads as mentioned above were soaked in a 20% ammonium fumarate solution (pH 8.3) overnight. 50 ml of the same was packed into a column and the column was externally covered with a thermal insulating material made of foamed polystyrene to maintain the internal temperature of the column constant. A substrate solution of Table 3 (which had been kept at 20° C. in a constant temperature water bath) was fed to the column through a Teflon tube wrapped with a thermal insulating material and made to flow through the column at a flow rate of 10 ml/hr (LHSV=0.2). Thus a continuous reaction was conducted.

10 hours after the reaction was started, the reaction solution was analyzed. As a result, it was found that L-aspartic acid approximately equimolar with the consumed fumaric acid was obtained as a reaction product, where the conversion rate of fumaric acid into L-aspartic acid was 99.0%.

To 1 liter of this reaction solution was added 29.3 g of a 25% aqueous ammonia solution. The reaction solution had a pH of 9.5. 90 g of fumaric acid was added to the reaction solution and stirred for 1 hour to give a suspension containing crystalline L-aspartic acid. At this point, the temperature of the suspension was 30° C. The suspension was filtrated and the resulting cake was fully compressed to remove liquid content therefrom. The cake was washed with 100 ml of water and then dried to give crystalline L-aspartic acid (yield 83.1 g; purity 98.7%).

Example 8

The recombinant immobilized aspartase beads as mentioned above were soaked in a 20% ammonium fumarate solution (pH 8.3) overnight. 50 ml of the same was packed into a column and the column was externally covered with a thermal insulating material made of foamed polystyrene to maintain the internal temperature of the column constant. A substrate solution of Table 3 (which had been kept at 20° C. in a constant temperature water bath) was fed to the column through a Teflon tube wrapped with a thermal insulating material and made to flow through the column at a flow rate of 500 ml/hr (LHSV=10.0). Thus a continuous reaction was conducted.

3 hours after the reaction was started, the reaction solution was analyzed. As a result, it was found that L-aspartic acid approximately equimolar with the consumed fumaric acid was obtained as a reaction product, where the conversion rate of fumaric acid into L-aspartic acid was 99.2%.

To 3 liters of this reaction solution was added 87.9 g of a 25% aqueous ammonia solution. The reaction solution had a pH of 9.5. 270 g of fumaric acid was added to the reaction solution and stirred for 1 hour to give a suspension containing crystalline L-aspartic acid. At this point, the temperature of the suspension was 30° C. The suspension was filtrated and the resulting cake was fully compressed to remove liquid content therefrom. The cake was washed with 300 ml of water and then dried to give crystalline L-aspartic acid (yield 252.4 g; purity 98.7%). The filtrate given after removing the crystals and the solution used for washing the resulting cake were combined and condensed under reduced pressure. The solution was supplemented with 70.0 g of a 25% aqueous ammonia solution and made up with deionized water to 3 liters.

This solution was re-used as the starting substrate solution for the subsequent reaction. That is, the solution (which had been kept at 20° C. in a constant temperature water bath) was fed to the column through a Teflon tube wrapped with a thermal insulating material and made to flow through the column at a flow rate of 500 ml/hr (LHSV=10.0). Thus a continuous reaction was conducted.

Thirty minutes after the reaction was started, the reaction solution was analyzed. As a result, it was found that L-aspartic acid approximately equimolar with the consumed fumaric acid was obtained as a reaction product, where the conversion rate of fumaric acid into L-aspartic acid was 99.2%.

2 liters of this reaction solution was removed and 58.6 g of a 25% aqueous ammonia solution was added thereto. The reaction solution had a pH of 9.5. 180 g of fumaric acid was added to the reaction solution and stirred for 1 hour to give a suspension containing crystalline L-aspartic acid. At this point, the temperature of the suspension was 30° C. The suspension was filtrated and the resulting cake was fully compressed to remove liquid content therefrom. The cake was washed with 200 ml of water and then dried to give crystalline L-aspartic acid (yield 189.3 g; purity 98.7%). The filtrate given after removing the crystals and the solution used for washing the cake were combined and condensed under reduced pressure. The solution was supplemented with 46.7 g of a 25% aqueous ammonia solution and made up with deionized water to 2 liters.

This solution was re-used as the starting substrate solution for the subsequent reaction. That is, the solution (which had been kept at 20° C. in a constant temperature water bath) was fed to the column through a Teflon tube wrapped with a thermal insulating material and made to flow through the column at a flow rate of 500 ml/hr (LHSV=10.0). Thus a continuous reaction was conducted.

Thirty minutes after the reaction was started, the reaction solution was analyzed. As a result, it was found that L-aspartic acid approximately equimolar with the consumed fumaric acid was obtained as a reaction product, where the conversion rate of fumaric acid into L-aspartic acid was 99.2%.

1 liter of this reaction solution was removed and 29.3 g of a 25% aqueous ammonia solution was added thereto. The reaction solution had a pH of 9.5. 90 g of fumaric acid was added to the reaction solution and stirred for 1 hour to give a suspension containing crystalline L-aspartic acid. At this point, the temperature of the suspension was 30° C. The suspension was filtrated and the resulting cake was fully compressed to remove liquid content therefrom. The cake was washed with 200 ml of water and then dried to give crystalline L-aspartic acid (yield 95.9 g; purity 98.7%).

Example 9

The recombinant immobilized aspartase beads as mentioned above were soaked in a 20% ammonium fumarate solution (pH 8.3) overnight. 50 ml of the same was packed into a column and the column was externally covered with a thermal insulating material made of foamed polystyrene to maintain the internal temperature of the column constant. A substrate solution of Table 3 (which had been kept at 20° C. in a constant temperature water bath) was fed to the column through a Teflon tube wrapped with a thermal insulating material and made to flow through the column at a flow rate of 500 ml/hr (LHSV=10.0). Thus a continuous reaction was conducted.

3 hours after the reaction was started, the reaction solution was analyzed. As a result, it was found that L-aspartic acid approximately equimolar with the consumed fumaric acid was obtained as a reaction product, where the conversion rate of fumaric acid into L-aspartic acid was 99.2%.

To 1 liter of the reaction solution were added 29.3 g of a 25% aqueous ammonia solution and subsequently 50 g (0.5 mole) of fumaric acid was added. The reaction mixture was stirred for 1 hour to give a suspension containing crystalline L-aspartic acid. At this point, the temperature of the suspension was 30° C. The suspension was filtrated and the resulting cake was fully compressed to remove liquid content therefrom. The cake was washed with 100 ml of water and then dried to give crystalline L-aspartic acid (yield 51.6 g; purity 98.8%).

Example 10

The recombinant immobilized aspartase beads as mentioned above were soaked in a 20% ammonium fumarate solution (pH 8.3) overnight. 50 ml of the same was packed into a column and the column was externally covered with a thermal insulating material made of foamed polystyrene to maintain the internal temperature of the column constant. A substrate solution of Table 5 (which had been kept at 20° C. in a constant temperature water bath) was fed to the column through a Teflon tube wrapped with a thermal insulating material and made to flow through the column at a flow rate of 100 ml/hr (LHSV=2.0). Thus a continuous reaction was conducted.

3 hours after the reaction was started, the reaction solution was analyzed. As a result, it was found that L-aspartic acid approximately equimolar with the consumed fumaric acid was obtained as a reaction product, where the conversion rate of fumaric acid into L-aspartic acid was 10.8%.

TABLE 5

| Fumaric acid | 100 g |
|---|---|
| NaOH | 69.0 g |
| (2.0 times the molar amount of fumaric acid) | |
| 25% Aqueous ammonia solution | 58.4 g |
| (1.0 times the molar amount of fumaric acid) | |
| Magnesium sulfate | 0.25 g |
| (made up with deionized water to 1 liter). | |

Example 11

The recombinant immobilized aspartase beads as mentioned above were soaked in a 20% ammonium fumarate solution (pH 8.3) overnight. 50 ml of the same was packed into a column and the column was externally covered with a thermal insulating material made of foamed polystyrene to maintain the internal temperature of the column constant. A substrate solution of Table 6 (which had been kept at 20° C. in a constant temperature water bath) was fed to the column through a Teflon tube wrapped with a thermal insulating material and made to flow through the column at a flow rate of 100 ml/hr (LHSV=2.0). Thus a continuous reaction was conducted.

3 hours after the reaction was started, the reaction solution was analyzed. As a result, it was found that L-aspartic acid approximately equimolar with the consumed fumaric acid was obtained as a reaction product, where the conversion rate of fumaric acid into L-aspartic acid was 80.2%.

TABLE 6

| Fumaric acid | 100 g |
|---|---|
| NaOH | 60 g |
| (1.74 times the molar amount of fumaric acid) | |
| 25% Aqueous ammonia solution | 58.4 g |
| (1.0 times the molar amount of fumaric acid) | |
| Magnesium sulfate | 0.25 g |
| (made up with deionized water to 1 liter) | |

Comparative Example 1

The recombinant immobilized aspartase beads as mentioned above were soaked in a 20% ammonium fumarate solution (pH 8.3) overnight. 50 ml of the same was packed into a column and the column was externally covered with a thermal insulating material made of foamed polystyrene to maintain the internal temperature of the column constant. A substrate solution of Table 7 (which had been kept at 20° C. in a constant temperature water bath) was fed to the column through a Teflon tube wrapped with a thermal insulating material and made to flow through the column at a flow rate of 500 ml/hr (LHSV=10.0). Thus a continuous reaction was conducted.

3 hours after the reaction was started, the reaction solution was analyzed. As a result, it was found that L-aspartic acid approximately equimolar with the consumed fumaric acid was obtained as a reaction product, where the conversion rate of fumaric acid into L-aspartic acid was 99.7%.

To 1 liter of this reaction solution were added 58.6 g of a 25% aqueous ammonia solution and subsequent 100 g of fumaric acid. The reaction mixture was stirred for 1 hour to give a suspension containing crystalline L-aspartic acid. The suspension was filtered and the resulting cake was fully compressed to remove liquid content therefrom. The cake was washed with 100 ml of water and then dried to give crystalline L-aspartic acid (yield 56.1 g; purity 98.7%).

TABLE 7

| | |
|---|---|
| Fumaric acid | 100 g |
| 25% Aqueous ammonia solution | 129.0 g |
| (2.2 times the molar amount of fumaric acid) | |
| Magnesium sulfate | 0.25 g |
| (made up with deionized water to 1 liter). | |

As is evident from this result, the reaction without NaOH results in production of crystalline L-aspartic acid in a poor yield.

Example 12

The recombinant immobilized aspartase beads as mentioned above were soaked in a 20% ammonium fumarate solution (pH 8.3) overnight. 50 ml of the same was packed into a column and the column was externally covered with a thermal insulating material made of foamed polystyrene to maintain the internal temperature of the column constant. A substrate solution of Table 8 (which had been kept at 20° C. in a constant temperature water bath) was fed to the column through a Teflon tube wrapped with a thermal insulating material and made to flow through the column at a flow rate of 500 ml/hr (LHSV=10.0). Thus a continuous reaction was conducted.

3 hours after the reaction was started, the reaction solution was analyzed. As a result, it was found that L-aspartic acid approximately equimolar with the consumed fumaric acid was obtained as a reaction product, where the conversion rate of fumaric acid into L-aspartic acid was 99.4%.

To 1 liter of this reaction solution was added 14.7 g of a 25% aqueous ammonia solution. The reaction solution had a pH of 9.1. 70 g of fumaric acid was added to the reaction solution and stirred for 1 hour to give a suspension containing crystalline L-aspartic acid. At this point, the temperature of the suspension was 30° C. The suspension was filtered and the resulting cake was fully compressed to remove liquid content therefrom. The cake was washed with 100 ml of water and then dried to give crystalline L-aspartic acid (yield 30.1 g; purity 98.8%).

TABLE 8

| | |
|---|---|
| Fumaric acid | 100 g |
| NaOH | 10 g |
| (0.29 times the molar amount of fumaric acid) | |
| 25% Aqueous ammonia solution | 102.6 g |
| (1.75 times the molar amount of fumaric acid) | |
| Magnesium sulfate | 0.25 g |
| (made up with deionized water to 1 liter). | |

Example 13

The non-recombinant immobilized aspartase beads prepared as mentioned above were soaked in a 20% ammonium fumarate solution (pH 8.3) overnight. 50 ml of the same was packed into a column and the column was externally covered with a thermal insulating material made of foamed polystyrene to maintain the internal temperature of the column constant. A substrate solution of Table 3 (which had been kept at 20° C. in a constant temperature water bath) was fed to the column through a Teflon tube wrapped with a thermal insulating material and made to flow through the column at a flow rate of 100 ml/hr (LHSV=2.0). Thus a continuous reaction was conducted.

3 hours after the reaction was started, the reaction solution was analyzed. As a result, it was found that L-aspartic acid approximately equimolar with the consumed fumaric acid was obtained as a reaction product, where the conversion rate of fumaric acid into L-aspartic acid was 80.2%.

Example 14

The recombinant immobilized aspartase beads as mentioned above were soaked in a 20% ammonium fumarate solution (pH 8.3) overnight. 50 ml of the same was packed into a column and the column was externally covered with a thermal insulating material made of foamed polystyrene to maintain the internal temperature of the column constant. A substrate solution of Table 3 (which had been kept at 20° C. in a constant temperature water bath) was fed to the column through a Teflon tube wrapped with a thermal insulating material and made to flow through the column at a flow rate of 500 ml/hr (LHSV=10.0). Thus a continuous reaction was conducted.

3 hours after the reaction was started, the reaction solution was analyzed. As a result, it was found that L-aspartic acid approximately equimolar with the consumed fumaric acid was obtained as a reaction product, where the conversion rate of fumaric acid into L-aspartic acid was 99.2%.

To 1 liter of this reaction solution was added 29.3 g of a 25% aqueous ammonia solution. The reaction solution had a pH of 9.5. The reaction solution was heated to 60° C. and then 70 g of fumaric acid was added thereto. The reaction mixture was stirred to give a homogeneous solution in which the crystals of fumaric acid were dissolved completely. The solution was gradually cooled while stirring. At the temperature around 45° C., crystals of L-aspartic acid came to appear in the solution. The suspension was further cooled to 30° C. and stirring was allowed to continue at that temperature for additional 30 min. The suspension was filtered and the resulting cake was fully compressed to remove liquid content therefrom. The cake was washed with 100 ml of water and then dried to give crystalline L-aspartic acid (yield 59.7 g; purity 99.1%).

Example 15

The recombinant immobilized aspartase beads as mentioned above were soaked in a 20% ammonium fumarate solution (pH 8.3) overnight. 50 ml of the same was packed into a column and the column was externally covered with a thermal insulating material made of foamed polystyrene to maintain the internal temperature of the column constant. A substrate solution of Table 3 (which had been kept at 20° C. in a constant temperature water bath) was fed to the column through a Teflon tube wrapped with a thermal insulating material and made to flow through the column at a flow rate of 500 ml/hr (LHSV=10.0). Thus a continuous reaction was conducted.

3 hours after the reaction was started, the reaction solution was analyzed. As a result, it was found that L-aspartic acid approximately equimolar with the consumed fumaric acid was obtained as a reaction product, where the conversion rate of fumaric acid into L-aspartic acid was 99.2%.

To 1 liter of this reaction solution was added 29.3 g of a 25% aqueous ammonia solution. The reaction solution had a pH of 9.5. The reaction solution was heated to 60° C. and then 80 g of fumaric acid was added thereto. The reaction mixture was stirred to give a homogeneous solution in which the crystals of fumaric acid were dissolved completely. The solution was gradually cooled while stirring. At the temperature around 45° C., crystals of L-aspartic acid came to appear in the solution. The suspension was further cooled to 30° C. and stirring was allowed to continue at that temperature for additional 30 min. The suspension was filtrated and the resulting cake was fully compressed to remove liquid content therefrom. The cake was washed with 100 ml of water and then dried to give crystalline L-aspartic acid (yield 71.2 g; purity 99.1%).

Example 16

The recombinant immobilized aspartase beads as mentioned above were soaked in a 20% ammonium fumarate solution (pH 8.3) overnight. 50 ml of the same was packed into a column and the column was externally covered with a thermal insulating material made of foamed polystyrene to maintain the internal temperature of the column constant. A substrate solution of Table 3 (which had been kept at 20° C. in a constant temperature water bath) was fed to the column through a Teflon tube wrapped with a thermal insulating material and made to flow through the column at a flow rate of 500 ml/hr (LHSV=10.0). Thus a continuous reaction was conducted.

3 hours after the reaction was started, the reaction solution was analyzed. As a result, it was found that L-aspartic acid approximately equimolar with the consumed fumaric acid was obtained as a reaction product, where the conversion rate of fumaric acid into L-aspartic acid was 99.2%.

To 1 liter of this reaction solution was added 29.3 g of a 25% aqueous ammonia solution. The reaction solution had a pH of 9.5. The reaction solution was heated to 60° C. and then 90 g of fumaric acid was added thereto. The reaction mixture was stirred to give a homogeneous solution in which the crystals of fumaric acid were dissolved completely. The solution was gradually cooled while stirring, whereby crystals of L-aspartic acid came to appear in the solution at about 45° C. The suspension was further cooled to 30° C. and stirring was allowed to continue at that temperature for additional 30 min. Ninety g of fumaric acid was added to the suspension and stirred for 1 hour. The suspension was filtrated and the resulting cake was fully compressed to remove liquid content therefrom. The cake was washed with 100 ml of water and then dried to give crystalline L-aspartic acid (yield 83.2 g; purity 99.1%).

Example 17

The recombinant immobilized aspartase beads as mentioned above were soaked in a 20% ammonium fumarate solution (pH 8.3) overnight. 50 ml of the same was packed into a column and the column was externally covered with a thermal insulating material made of foamed polystyrene to maintain the internal temperature of the column constant. A substrate solution of Table 3 (which had been kept at 20° C. in a constant temperature water bath) was fed to the column through a Teflon tube wrapped with a thermal insulating material and made to flow through the column at a flow rate of 500 ml/hr (LHSV=10.0). Thus a continuous reaction was conducted.

3 hours after the reaction was started, the reaction solution was analyzed. As a result, it was found that L-aspartic acid approximately equimolar with the consumed fumaric acid was obtained as a reaction product, where the conversion rate of fumaric acid into L-aspartic acid was 99.2%.

To 1 liter of this reaction solution was added 34.6 g of a 25% aqueous ammonia solution. The reaction solution had a pH of 9.8. The reaction solution was heated to 60° C. and then 100 g of fumaric acid was added thereto. The reaction mixture was stirred to give a homogeneous solution in which the crystals of fumaric acid were dissolved completely. The solution was gradually cooled while stirring, whereby crystals of L-aspartic acid came to appear in the solution at about 45° C. The suspension was further cooled to 30° C. and stirring was allowed to continue at that temperature for additional 30 min. The suspension was filtrated and the resulting cake was fully compressed to remove liquid content therefrom. The cake was washed with 100 ml of water and then dried to give crystalline L-aspartic acid (yield 93.6 g; purity 99.1%).

As is evident from the results of Examples 14–17 above, it is preferable to add 70 g or more of fumaric acid since a good recovery of L-aspartic acid of 60% or more can be attained.

Example 18

The recombinant immobilized aspartase beads as mentioned above were soaked in a 20% ammonium fumarate solution (pH 8.3) overnight. 50 ml of the same was packed into a column and the column was externally covered with a thermal insulating material made of foamed polystyrene to maintain the internal temperature of the column constant. A substrate solution of Table 4 (which had been kept at 20° C. in a constant temperature water bath) was fed to the column through a Teflon tube wrapped with a thermal insulating material and made to flow through the column at a flow rate of 500 ml/hr (LHSV=10.0). Thus a continuous reaction was conducted.

3 hours after the reaction was started, the reaction solution was analyzed. As a result, it was found that L-aspartic acid approximately equimolar with the consumed fumaric acid was obtained as a reaction product, where the conversion rate of fumaric acid into L-aspartic acid was 99.2%.

To 1 liter of this reaction solution was added 17.6 g of a 25% aqueous ammonia solution. The reaction solution had a pH of 9.1. The reaction solution was heated to 60° C. and then 70 g of fumaric acid was added thereto. The reaction mixture was stirred to give a homogeneous solution in which the crystals of fumaric acid were dissolved completely. The solution was gradually cooled while stirring, whereby crystals of L-aspartic acid came to appear in the solution at about 45° C. The suspension was further cooled to 30° C. and stirring was allowed to continue at that temperature for additional 30 min. The suspension was filtrated and the resulting cake was fully compressed to remove liquid content therefrom. The cake was washed with 100 ml of water and the crystals obtained were dried to give crystalline L-aspartic acid (yield 87.1 g; purity 99.0%).

Example 19

The recombinant immobilized aspartase beads as mentioned above were soaked in a 20% ammonium fumarate solution (pH 8.3) overnight. 50 ml of the same was packed into a column and the column was externally covered with a thermal insulating material made of foamed polystyrene to maintain the internal temperature of the column constant. A substrate solution of Table 4 (which had been kept at 20° C. in a constant temperature water bath) was fed to the column through a Teflon tube wrapped with a thermal insulating material and made to flow through the column at a flow rate of 500 ml/hr (LHSV=10.0). Thus a continuous reaction was conducted.

3 hours after the reaction was started, the reaction solution was analyzed. As a result, it was found that L-aspartic acid approximately equimolar with the consumed fumaric acid was obtained as a reaction product, where the conversion rate of fumaric acid into L-aspartic acid was 99.2%.

To 1 liter of this reaction solution was added 17.6 g of a 25% aqueous ammonia solution. The reaction solution had a pH of 9.1. The reaction solution was heated to 60° C. and then 90 g of fumaric acid was added thereto. The reaction mixture was stirred to give a homogeneous solution in which the crystals of fumaric acid were dissolved completely. The solution was gradually cooled while stirring, whereby crystals of L-aspartic acid came to appear in the solution at about 45° C. The suspension was further cooled to 30° C. and stirring was allowed to continue at that temperature for additional 30 min. The suspension was filtrated and the resulting cake was fully compressed to remove liquid content therefrom. The cake was washed with 100 ml of water and then dried to give crystalline L-aspartic acid (yield 96.7 g; purity 98.5%).

Example 20

The non-recombinant immobilized aspartase beads prepared as mentioned above were soaked in a 20% ammonium fumarate solution (pH 8.3) overnight. 50 ml of the same was packed into a column and the column was externally covered with a thermal insulating material made of foamed polystyrene to maintain the internal temperature of the column constant. A substrate solution of Table 3 (which had been kept at 20° C. in a constant temperature water bath) was fed to the column through a Teflon tube wrapped with a thermal insulating material and made to flow through the column at a flow rate of 10 ml/hr (LHSV=0.2). Thus a continuous reaction was conducted.

10 hours after the reaction was started, the reaction solution was analyzed. As a result, it was found that L-aspartic acid approximately equimolar with the consumed fumaric acid was obtained as a reaction product, where the conversion rate of fumaric acid into L-aspartic acid was 99.0%.

To 1 liter of this reaction solution was added 29.3 g of a 25% aqueous ammonia solution. The reaction solution had a pH of 9.5. The reaction solution was heated to 60° C. and then 90 g of fumaric acid was added thereto. The reaction mixture was stirred to give a homogeneous solution in which the crystals of fumaric acid were dissolved completely. The solution was gradually cooled while stirring, whereby crystals of L-aspartic acid came to appear in the solution at about 45° C. The suspension was further cooled to 30° C. and stirring was allowed to continue at that temperature for additional 30 min. The suspension was filtrated and the resulting cake was fully compressed to remove liquid content therefrom. The cake was washed with 100 ml of water and then dried to give crystalline L-aspartic acid (yield 82.8 g; purity 99.2%).

Example 21

The recombinant immobilized aspartase beads as mentioned above were soaked in a 20% ammonium fumarate solution (pH 8.3) overnight. 50 ml of the same was packed into a column and the column was externally covered with a thermal insulating material made of foamed polystyrene to maintain the internal temperature of the column constant. A substrate solution of Table 3 (which had been kept at 20° C. in a constant temperature water bath) was fed to the column through a Teflon tube wrapped with a thermal insulating material and made to flow through the column at a flow rate of 500 ml/hr (LHSV=10.0). Thus a continuous reaction was conducted.

3 hours after the reaction was started, the reaction solution was analyzed. As a result, it was found that L-aspartic acid approximately equimolar with the consumed fumaric acid was obtained as a reaction product, where the conversion rate of fumaric acid into L-aspartic acid was 99.2%.

To 3 liters of this reaction solution was added 87.9 g of a 25% aqueous ammonia solution. The reaction solution had a pH of 9.5. The reaction solution was heated to 60° C. and then 270 g of fumaric acid was added thereto. The reaction mixture was stirred to give a homogeneous solution in which the crystals of fumaric acid were dissolved completely. The solution was gradually cooled while stirring, whereby crystals of L-aspartic acid came to appear in the solution at about 45° C. The suspension was further cooled to 30° C. and stirring was allowed to continue at that temperature for additional 30 min. The suspension was filtrated and the resulting cake was fully compressed to remove liquid content therefrom. The cake was washed with 300 ml of water and then dried to give crystalline L-aspartic acid (yield 251.1 g; purity 99.2%). The filtrate given after removing the crystals and the solution used for washing the cake were combined and condensed under reduced pressure. The solution was supplemented with 70.0 g of a 25% aqueous ammonia solution and made up with deionized water to 3 liters.

This solution was re-used as the starting substrate solution for the subsequent reaction. That is, the solution (which had been kept at 20° C. in a constant temperature water bath) was fed to the column through a Teflon tube wrapped with a thermal insulating material and made to flow through the column at a flow rate of 500 ml/hr (LHSV=10.0). Thus a continuous reaction was conducted.

Thirty minutes after the reaction was started, the reaction solution was analyzed. As a result, it was found that L-aspartic acid approximately equimolar with the consumed fumaric acid was obtained as a reaction product, where the conversion rate of fumaric acid into L-aspartic acid was 99.2%.

At this point in time, 2 liters of this reaction solution was removed and 58.6 g of a 25% aqueous ammonia solution was added thereto. The reaction solution had a pH of 9.5. The reaction solution was heated to 60° C. and then 180 g of fumaric acid was added thereto. The reaction mixture was stirred to give a homogeneous solution in which the crystals of fumaric acid were dissolved completely. The solution was gradually cooled while stirring, whereby crystals of L-aspartic acid came to appear in the solution at about 45° C. The suspension was further cooled to 30° C. and stirring was allowed to continue at that temperature for additional 30 min. The suspension was filtrated and the resulting cake was fully compressed to remove liquid content therefrom. The cake was washed with 200 ml of water and then dried to give crystalline L-aspartic acid (yield 188.6 g; purity 99.2%). The filtrate given after removing the crystals and the solution used for washing the cake were combined and condensed under reduced pressure. The solution was supplemented with 46.7 g of a 25% aqueous ammonia solution and made up with deionized water to 2 liters.

This solution was re-used as the starting substrate solution for the subsequent reaction. That is, the solution (which had been kept at 20° C. in a constant temperature water bath) was fed to the column through a Teflon tube wrapped with a thermal insulating material and made to flow through the column at a flow rate of 500 ml/hr (LHSV=10.0). Thus a continuous reaction was conducted.

Thirty minutes after the reaction was started, the reaction solution was analyzed. As a result, it was found that L-aspartic acid approximately equimolar with the consumed fumaric acid was obtained as a reaction product, where the conversion rate of fumaric acid into L-aspartic acid was 99.2%.

At this point in time, 1 liter of this reaction solution was removed and 29.3 g of a 25% aqueous ammonia solution was added thereto. The reaction solution had a pH of 9.5. The reaction solution was heated to 60° C. and then 90 g of fumaric acid was added thereto. The reaction mixture was stirred to give a homogeneous solution in which the crystals of fumaric acid were dissolved completely. The solution was gradually cooled while stirring, whereby crystals of L-aspartic acid came to appear in the solution at about 45° C. The suspension was further cooled to 30° C. and stirring was allowed to continue at that temperature for additional 30 min. The suspension was filtrated and the resulting cake was fully compressed to remove liquid content therefrom. The cake was washed with 200 ml of water and then dried to give crystalline L-aspartic acid (yield 95.6 g; purity 99.2%).

Example 22

The recombinant immobilized aspartase beads as mentioned above were soaked in a 20% ammonium fumarate solution (pH 8.3) overnight. 50 ml of the same was packed into a column and the column was externally covered with a thermal insulating material made of foamed polystyrene to maintain the internal temperature of the column constant. A substrate solution of Table 3 (which had been kept at 20° C. in a constant temperature water bath) was fed to the column through a Teflon tube wrapped with a thermal insulating material and made to flow through the column at a flow rate of 500 ml/hr (LHSV=10.0). Thus a continuous reaction was conducted.

3 hours after the reaction was started, the reaction solution was analyzed. As a result, it was found that L-aspartic acid approximately equimolar with the consumed fumaric acid was obtained as a reaction product, where the conversion rate of fumaric acid into L-aspartic acid was 99.2%.

To 1 liter of this reaction solution was added 29.3 g of a 25% aqueous ammonia solution. The reaction solution was heated to 60° C. and then 50 g (0.5 mole) of fumaric acid was added thereto. The reaction mixture was stirred to give a homogeneous solution in which the crystals of fumaric acid were dissolved completely. The solution was gradually cooled while stirring, whereby crystals of L-aspartic acid came to appear in the solution at about 45° C. The suspension was further cooled to 30° C. and stirring was allowed to continue at that temperature for additional 30 min. The suspension was filtrated and the resulting cake was fully compressed to remove liquid content therefrom. The cake was washed with 100 ml of water and then dried to give crystalline L-aspartic acid (yield 50.3 g; purity 99.3%).

Comparative Example 2

The recombinant immobilized aspartase beads as mentioned above were soaked in a 20% ammonium fumarate solution (pH 8.3) overnight. 50 ml of the same was packed into a column and the column was externally covered with a thermal insulating material made of foamed polystyrene to maintain the internal temperature of the column constant. A substrate solution of Table 7 (which had been kept at 20° C. in a constant temperature water bath) was fed to the column through a Teflon tube wrapped with a thermal insulating material and made to flow through the column at a flow rate of 500 ml/hr (LHSV=10.0). Thus a continuous reaction was conducted.

3 hours after the reaction was started, the reaction solution was analyzed. As a result, it was found that L-aspartic acid approximately equimolar with the consumed fumaric acid was obtained as a reaction product, where the conversion rate of fumaric acid into L-aspartic acid was 99.7%.

To 1 liter of this reaction solution was added 58.6 g of a 25% aqueous ammonia solution. The reaction solution was heated to 60° C. and then 100 g of fumaric acid was added thereto. The reaction mixture was stirred to give a homogeneous solution in which the crystals of fumaric acid were dissolved completely. The solution was gradually cooled while stirring, whereby crystals of L-aspartic acid came to appear in the solution at about 45° C. The suspension was further cooled to 30° C. and stirring was allowed to continue at that temperature for additional 30 min. The suspension was filtrated and the resulting cake was fully compressed to remove liquid content therefrom. The cake was washed with 100 ml of water and then dried to give crystalline L-aspartic acid (yield 55.5 g; purity 99.2%).

As is evident from this result, the reaction without NaOH results in production of crystalline L-aspartic acid in a poor yield.

Example 23

The recombinant immobilized aspartase beads as mentioned above were soaked in a 20% ammonium fumarate solution (pH 8.3) overnight. 50 ml of the same was packed into a column and the column was externally covered with a thermal insulating material made of foamed polystyrene to maintain the internal temperature of the column constant. A substrate solution of Table 8 (which had been kept at 20° C. in a constant temperature water bath) was fed to the column through a Teflon tube wrapped with a thermal insulating material and made to flow through the column at a flow rate of 500 ml/hr (LHSV=10.0). Thus a continuous reaction was conducted.

3 hours after the reaction was started, the reaction solution was analyzed. As a result, it was found that L-aspartic acid approximately equimolar with the consumed fumaric acid was obtained as a reaction product, where the conversion rate of fumaric acid into L-aspartic acid was 99.4%.

To 1 liter of this reaction solution was added 14.7 g of a 25% aqueous ammonia solution. The reaction solution had a pH of 9.1. The reaction solution was heated to 60° C. and then 70 g of fumaric acid was added thereto. The reaction mixture was stirred to give a homogeneous solution in which the crystals of fumaric acid were dissolved completely. The solution was gradually cooled while stirring, whereby crystals of L-aspartic acid came to appear in the solution at about 45° C. The suspension was further cooled to 30° C. and stirring was allowed to continue at that temperature for additional 30 min. The suspension was filtrated and the resulting cake was fully compressed to remove liquid content therefrom. The cake was washed with 100 ml of water and then dried to give crystalline L-aspartic acid (yield 29.3 g; purity 99.4%).

As mentioned above, according to the present invention, it becomes possible to produce crystalline L-aspartic acid of high purity in a good workability without the need of any complicated steps.

The invention has been described in detail with reference to various embodiments, and it will now be apparent from the foregoing to those skilled in the art that changes and modifications may be made without departing from the invention in its broader aspects, and it is the invention, therefore, in the appended claims to cover all such changes and modifications as fall within the true spirit of the invention.

All publications, patents and patent applications cited herein are incorporated herein by reference in their entirety.

The followings are information on sequences described herein:

What is claimed is:

1. A process for producing crystalline L-aspartic acid comprising
preparing a mix solution comprising fumaric acid, ammonia and an alkaline metal hydroxide,
reacting the mix solution with aspartase to give a reaction solution containing L-aspartate and crystallizing L-aspartic acid out of the reaction solution, wherein a further amount of ammonia is added to the reaction solution containing L-aspartate and subsequently fumaric acid is added thereto to crystallize L-aspartic acid.

2. The process as claimed in claim 1, wherein the non-crystallized aspartic acid remaining in the reaction solution after the crystallization of L-aspartic acid is isolated, ammonia is added to the solution, and the resultant solution is recycled as a part of the starting reaction solution for the process of producing crystalline L-aspartic acid.

3. A process for producing crystalline L-aspartic acid comprising:
preparing a mix solution comprising fumaric acid, ammonium L-aspartate, ammonia and an alkaline metal hydroxide,
reacting the mix solution with aspartase to give a reaction solution containing L-aspartate and crystallizing L-aspartic acid out of the reaction solution, wherein a further amount of ammonia is added to the reaction solution containing L-aspartate and subsequently fumaric acid is added thereto to crystallize L-aspartic acid.

4. A process for producing crystalline L-aspartic acid comprising:
preparing a mix solution comprising fumaric acid, ammonia and an alkaline metal hydroxide,
reacting the mix solution with aspartase to give a reaction solution containing L-aspartate and crystallizing L-aspartic acid out of the reaction solution, wherein a further amount of ammonia is added to the reaction solution containing L-aspartate, the reaction solution is heated, fumaric acid is added to the reaction solution, and the reaction solution is cooled to crystallize L-aspartic acid.

5. The process as claimed in claim 4, wherein the non-crystallized aspartic acid remaining in the reaction solution after the crystallization of L-aspartic acid is isolated, ammonia is added to the solution, and the resultant solution is recycled as a part of the starting reaction solution for the process of producing crystalline L-aspartic acid.

6. A process for producing crystalline L-aspartic acid comprising:
preparing a mix solution comprising fumaric acid, ammonium L-aspartate, ammonia and an alkaline metal hydroxide,
reacting the mix solution with aspartase to give a reaction solution containing L-aspartate and crystallizing L-aspartic acid out of the reaction solution, wherein a further amount of ammonia is added to the reaction solution containing L-aspartate, the reaction solution is heated, fumaric acid is added thereto to the reaction solution, and the reaction solution is cooled to crystallize L-aspartic acid.

7. The process as claimed in any one of claims 1, 3, 4, or 6, wherein the amount of the alkaline metal hydroxide in the mix solution is from 0.1 to 1 times the total molar amount of fumarate and L-aspartate both contained in the solution.

8. The process as claimed in any one of claims 1, 3, 4, or 6, wherein the amount of the fumaric acid added for crystallization of L-aspartic acid is from 0.6 to 1.2 times the total molar amount of fumarate and L-aspartate both contained in the reaction solution containing L-aspartic acid.

9. The process as claimed in any one of claims 1, 3, 4, or 6, wherein the aspartase is an immobilized aspartase prepared by immobilizing a transformant carrying an aspartase gene or a product from the transformant onto a carrier.

10. The process as claimed in any one of claims 1, 3, 4, or 6, wherein the mix solution contains fumaric acid and L-aspartic acid in a concentration of 8 to 20% in terms of fumaric acid, and wherein the mix solution is made to flow through a reactor containing an immobilized aspartase having an aspartase activity of 250 U of the carrier or more at a liquid hour space velocity of 2 to 20.

11. The process as claimed in any one of claims 1, 3, 4, or 6, wherein the aspartase is an immobilized aspartase prepared by adsorption of microorganism cells having an aspartase activity or products from the microorganism cells onto an ion exchange resin or by coating of a polymer containing the microorganism cells or the products from the microorganism cells onto the ion exchange resin.

12. The process as claimed in any one of claims 1, 3, 4, or 6, wherein the aspartase is an immobilized aspartase prepared by mixing microorganism cells having an aspartase activity or products from the microorganism cells with a polymer of formula (I) and then coating the mixture onto the surface of the spherical styrene/divinylbenzene copolymer ion exchange resin particles:

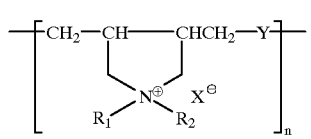
wherein Y denotes a direct bonding or a divalent group selected from the group consisting of
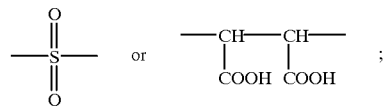
each of $R_1$ and $R_2$ is independently a hydrogen atom or an organic residue; $X^{\ominus}$ denotes an ion; and n is an integer from 100 to 5000.
* * * * *

UNITED STATES PATENT AND TRADEMARK OFFICE
CERTIFICATE OF CORRECTION

PATENT NO.:     6,150,142
DATED:          November 21, 2000
INVENTOR(S):    Mukouyama et al.

It is certified that an error appears in the above-identified patent and that said Letters Patent is hereby corrected as shown below:

In Claim 12, col. 33, line 12, after "consisting of", delete "or".

Signed and Sealed this

Twenty-ninth Day of May, 2001

*Attest:*

NICHOLAS P. GODICI

*Attesting Officer*     Acting Director of the United States Patent and Trademark Office

SEQUENCE LISTING

<160> NUMBER OF SEQ ID NOS: 3

<210> SEQ ID NO 1
<211> LENGTH: 1573
<212> TYPE: DNA
<213> ORGANISM: Escherichia coli

<400> SEQUENCE: 1

| | | |
|---|---|---|
| ggggataatc gtcggtcgaa aaacattcga aaccacatat attctgtgtg tttaaagcaa | 60 | |
| atcattggca gcttgaaaaa gaaggttcac atg tca aac aac att cgt atc gaa | 114 | |
|                                               Met Ser Asn Asn Ile Arg Ile Glu | | |
|                                               1                5 | | |
| gaa gat ctg ttg ggt acc agg gaa gtt cca gct gat gcc tac tat ggt | 162 | |
| Glu Asp Leu Leu Gly Thr Arg Glu Val Pro Ala Asp Ala Tyr Tyr Gly | | |
|     10                 15                20 | | |
| gtt cac act ctg aga gcg att gta aac ttc tat atc agc aac aac aaa | 210 | |
| Val His Thr Leu Arg Ala Ile Val Asn Phe Tyr Ile Ser Asn Asn Lys | | |
| 25                  30                35                40 | | |
| atc agt gat att cct gaa ttt gtt cgc ggt atg gta atg gtt aaa aaa | 258 | |
| Ile Ser Asp Ile Pro Glu Phe Val Arg Gly Met Val Met Val Lys Lys | | |
|                 45                50                55 | | |
| gcc gca gct atg gca aac aaa gag ctg caa acc att cct aaa agt gta | 306 | |
| Ala Ala Ala Met Ala Asn Lys Glu Leu Gln Thr Ile Pro Lys Ser Val | | |
|             60                  65                70 | | |
| gcg aat gcc atc att gcc gca tgt gat gaa gtc ctg aac aac gga aaa | 354 | |
| Ala Asn Ala Ile Ile Ala Ala Cys Asp Glu Val Leu Asn Asn Gly Lys | | |
|                 75                80                85 | | |
| tgc atg gat cag ttc ccg gta gac gtc tac cag ggc ggc gca ggt act | 402 | |
| Cys Met Asp Gln Phe Pro Val Asp Val Tyr Gln Gly Gly Ala Gly Thr | | |
|     90                 95                100 | | |
| tcc gta aac atg aac acc aac gaa gtg ctg gcc aat atc ggt ctg gaa | 450 | |
| Ser Val Asn Met Asn Thr Asn Glu Val Leu Ala Asn Ile Gly Leu Glu | | |
| 105                110              115              120 | | |
| ctg atg ggt cac caa aaa ggt gaa tat cag tac ctg aac ccg aac gac | 498 | |
| Leu Met Gly His Gln Lys Gly Glu Tyr Gln Tyr Leu Asn Pro Asn Asp | | |
|                 125              130              135 | | |
| cat gtt aac aaa tgt cag tcc act aac gac gcc tac ccg acc ggt ttc | 546 | |
| His Val Asn Lys Cys Gln Ser Thr Asn Asp Ala Tyr Pro Thr Gly Phe | | |
|             140                145              150 | | |
| cgt atc gca gtt tac tct tcc ctg att aag ctg gta gat gcg att aac | 594 | |
| Arg Ile Ala Val Tyr Ser Ser Leu Ile Lys Leu Val Asp Ala Ile Asn | | |
|         155                160              165 | | |
| caa ctg cgt gaa ggc ttt gaa cgt aaa gct gtc gaa ttc cag gac atc | 642 | |
| Gln Leu Arg Glu Gly Phe Glu Arg Lys Ala Val Glu Phe Gln Asp Ile | | |
|     170                175              180 | | |
| ctg aaa atg ggt cgt acc cag ctg cag gac gca gta ccg atg acc ctc | 690 | |
| Leu Lys Met Gly Arg Thr Gln Leu Gln Asp Ala Val Pro Met Thr Leu | | |
| 185                190              195              200 | | |
| ggt cag gaa ttc cgc gct ttc agc atc ctg ctg aaa gaa gaa gtg aaa | 738 | |
| Gly Gln Glu Phe Arg Ala Phe Ser Ile Leu Leu Lys Glu Glu Val Lys | | |

-continued

|  |  |
|---|---:|
|             205                 210                 215 | |
| aac atc caa cgt acc gct gaa ctg ctg ctg gaa gtt aac ctt ggt gca<br>Asn Ile Gln Arg Thr Ala Glu Leu Leu Leu Glu Val Asn Leu Gly Ala<br>         220                  225                 230 | 786 |
| aca gca atc ggt act ggt ctg aac acg ccg aaa gag tac tct ccg ctg<br>Thr Ala Ile Gly Thr Gly Leu Asn Thr Pro Lys Glu Tyr Ser Pro Leu<br>   235                  240                 245 | 834 |
| gca gtg aaa aaa ctg gct gaa gtt act ggc ttc cca tgc gta ccg gct<br>Ala Val Lys Lys Leu Ala Glu Val Thr Gly Phe Pro Cys Val Pro Ala<br>250                  255                 260 | 882 |
| gaa gac ctg atc gaa gcg acc tct gac tgc ggc gct tat gtt atg gtt<br>Glu Asp Leu Ile Glu Ala Thr Ser Asp Cys Gly Ala Tyr Val Met Val<br>265                  270                 275                 280 | 930 |
| cac ggc gcg ctg aaa cgc ctg gct gtg aag atg tcc aaa atc tgt aac<br>His Gly Ala Leu Lys Arg Leu Ala Val Lys Met Ser Lys Ile Cys Asn<br>                285                 290                 295 | 978 |
| gac ctg cgc ttg ctc tct tca ggc cca cgt gcc ggc ctg aac gag atc<br>Asp Leu Arg Leu Leu Ser Ser Gly Pro Arg Ala Gly Leu Asn Glu Ile<br>   300                  305                 310 | 1026 |
| aac ctg ccg gaa ctg cag gcg ggc tct tcc atc atg cca gct aaa gta<br>Asn Leu Pro Glu Leu Gln Ala Gly Ser Ser Ile Met Pro Ala Lys Val<br>                315                 320                 325 | 1074 |
| aac ccg gtt gtt ccg gaa gtg gtt aac cag gta tgc ttc aaa gtc atc<br>Asn Pro Val Val Pro Glu Val Val Asn Gln Val Cys Phe Lys Val Ile<br>330                  335                 340 | 1122 |
| ggt aac gac acc act gtt acc atg gca gca gaa gca ggt cag ctg cag<br>Gly Asn Asp Thr Thr Val Thr Met Ala Ala Glu Ala Gly Gln Leu Gln<br>345                  350                 355                 360 | 1170 |
| ttg aac gtt atg gag ccg gtc att ggc cag gcc atg ttc gaa tcc gtt<br>Leu Asn Val Met Glu Pro Val Ile Gly Gln Ala Met Phe Glu Ser Val<br>                365                 370                 375 | 1218 |
| cac att ctg acc aac gct tgc tac aac ctg ctg gaa aaa tgc att aac<br>His Ile Leu Thr Asn Ala Cys Tyr Asn Leu Leu Glu Lys Cys Ile Asn<br>   380                  385                 390 | 1266 |
| ggc atc act gct aac aaa gaa gtg tgc gaa ggt tac gtt tac aac tct<br>Gly Ile Thr Ala Asn Lys Glu Val Cys Glu Gly Tyr Val Tyr Asn Ser<br>                395                 400                 405 | 1314 |
| atc ggt atc gtt act tac ctg aac ccg ttc atc ggt cac cac aac ggt<br>Ile Gly Ile Val Thr Tyr Leu Asn Pro Phe Ile Gly His His Asn Gly<br>   410                  415                 420 | 1362 |
| gac atc gtg ggt aaa atc tgt gcc gaa acc ggt aag agt gta cgt gaa<br>Asp Ile Val Gly Lys Ile Cys Ala Glu Thr Gly Lys Ser Val Arg Glu<br>425                  430                 435                 440 | 1410 |
| gtc gtt ctg gaa cgc ggt ctg ttg act gaa gcg gaa ctt gac gat att<br>Val Val Leu Glu Arg Gly Leu Leu Thr Glu Ala Glu Leu Asp Asp Ile<br>                445                 450                 455 | 1458 |
| ttc tcc gta cag aat ctg atg cac ccg gct tac aaa gca aaa cgc tat<br>Phe Ser Val Gln Asn Leu Met His Pro Ala Tyr Lys Ala Lys Arg Tyr<br>   460                  465                 470 | 1506 |
| act gat gaa agc gaa cag taatcgtaca gggtagtaca aataaaaaag<br>Thr Asp Glu Ser Glu Gln<br>                475 | 1554 |
| gcacgtcaga tgacgtgcc | 1573 |

<210> SEQ ID NO 2
<211> LENGTH: 20
<212> TYPE: DNA
<213> ORGANISM: Artificial Sequence
<220> FEATURE:
<223> OTHER INFORMATION: Designed primer based on aspartase gene -continued sequence of Escherichia coli K-12 strain (SEQ ID NO:1).

<400> SEQUENCE: 2
ggataatcgt cggtcgaaaa                                              20

<210> SEQ ID NO 3
<211> LENGTH: 19
<212> TYPE: DNA
<213> ORGANISM: Artificial Sequence
<220> FEATURE:
<223> OTHER INFORMATION: Designed primer based on aspartase gene
      sequence of Escherichia coli K-12 strain (SEQ ID NO:1).

<400> SEQUENCE: 3
cgtcatctga cgtgcctttt                                              19